(12) United States Patent
Morningstar

(10) Patent No.: US 8,939,890 B2
(45) Date of Patent: *Jan. 27, 2015

(54) IMPLANTABLE PENILE PROSTHESIS

(71) Applicant: Coloplast A/S, Humlebaek (DK)

(72) Inventor: Randy Lee Morningstar, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/273,548

(22) Filed: May 9, 2014

(65) Prior Publication Data

US 2014/0249366 A1    Sep. 4, 2014

Related U.S. Application Data

(60) Continuation of application No. 12/900,491, filed on Oct. 8, 2010, now Pat. No. 8,758,222, which is a division of application No. 12/430,117, filed on Apr. 27, 2009, now Pat. No. 7,833,149.

(30) Foreign Application Priority Data

Apr. 29, 2008   (DK) .................................. 2008 00602

(51) Int. Cl.
*A61F 2/26*    (2006.01)

(52) U.S. Cl.
CPC ........... *A61F 2/26* (2013.01); *A61F 2250/0003* (2013.01)

USPC .......................................................... 600/40

(58) Field of Classification Search
CPC ......... A61F 2/26; A61F 5/41; A61F 2005/41; A61F 2005/411; A61H 19/30; A61H 19/34; A61H 19/40; A61H 19/50; A61H 2201/165; A61H 2205/085
USPC ...................................................... 600/38–41
See application file for complete search history.

(56) References Cited

U.S. PATENT DOCUMENTS 5,062,416 A * 11/1991 Stucks ............................. 600/40

* cited by examiner

*Primary Examiner* — Samuel Gilbert
(74) *Attorney, Agent, or Firm* — Coloplast Corp. Coloplast A/S; Nick Baumann

(57) ABSTRACT

An implantable penile prosthesis is attachable to a pump and a reservoir and includes a distal part formed by a rear tip that is connected to a proximal part formed by a cylinder. The cylinder is oriented on a first longitudinal axis, and a distal portion of the rear tip forms a fluid chamber communicating with the cylinder. A tubing junction is integrally formed with the distal portion and communicates with the fluid chamber in the rear tip. A strain relief portion has a bore disposed on a second longitudinal axis, where the second longitudinal axis forms an acute angle relative to the first longitudinal axis, and the acute angle has a measurement that does not exceed 5 degrees. An exterior surface of the rear tip, between the tubing junction and the cylinder, provides the distal portion of the rear tip with a constant outer diameter.

9 Claims, 1 Drawing Sheet

IMPLANTABLE PENILE PROSTHESIS

FIELD OF THE INVENTION

The present invention relates generally to inflatable penile prostheses. The invention relates specifically to a low profile rear tip for inflatable penile prostheses.

BACKGROUND OF THE INVENTION

Inflatable penile prostheses (or, as may be termed hereinafter, "IPPs") are well known and have been in wide use. These devices are surgically implanted in male patients who, typically, are unable to achieve or sustain a penile erection due to a physical disability.

IPPs typically comprise several components such as a fluid reservoir, a pump, a valve, at least one inflatable cylinder including a rear tip with a strain relief portion and a tubing junction, and various lengths of tubing which fluidly connect the fluid reservoir, the pump, the valve, and the strain relief portion of the inflatable cylinder or cylinders (hereinafter, whether singular or plural, "cylinder"). Typically the fluid reservoir is surgically implanted in the patient's abdomen, with the pump and the inflatable cylinder being surgically implanted in, respectively, the patient's scrotum and penile corpora cavernosa; and the valve is commonly co-located with the scrotal pump. After implantation and in use, when an erection is desired by the patient, the scrotal pump is typically manipulated by the patient in an instructed way to cause fluid transfer by way of the tubing from the reservoir, via the valve, through the tubing junction, strain relief portion and rear tip, and to the cylinder such that inflation of the cylinder is effected thereby resulting in an erection as desired. When the patient desires to terminate the erection and return his penis to a flaccid state, the scrotal pump is typically again manipulated by the patient in an instructed way to cause fluid transfer from the cylinder through the rear tip and strain relief portion, through the tubing junction, via the valve, and back to the reservoir such that deflation of the cylinder is effected thereby resulting in penile flaccidity as desired. Regardless of a particular construction or mode of operation, various examples of IPPs per se and their components are described in U.S. Pat. No. 4,235,227 to Yamanaka, titled "Artificial Corpus Cavernosum Device; U.S. Pat. No. 4,566,446 to Fogarty, titled "Penile Prosthesis Device"; U.S. Pat. No. 4,782,826 to Fogarty, titled "Penile Prosthesis"; U.S. Pat. No. 5,062,417 to Cowen, titled "Prosthesis with Improved Pump"; U.S. Pat. No. 5,063,914 to Cowen, titled "Penile Prosthesis"; U.S. Pat. No. 5,067,485 to Cowen, titled "Corpus Cavernosum Implant Device"; U.S. Pat. No. 5,167,611 to Cow[e]n, titled "Penile Implant with Lengthening Cylinder"; U.S. Pat. No. 5,250,020 to Bley, titled "Unitary Inflatable Penile Prosthesis"; U.S. Pat. Nos. 5,851,176 and 6,171,233 to Willard, each titled "Pressure-Responsive Lockout Valve and Method of Use"; U.S. Pat. No. 5,895,424 to Steele, Sr., et al., titled "Prosthesis Having an Alignment Indicator and Method of Using Same"; and U.S. Pat. Nos. 6,808,490 and 7,169,103 to Ling, et al., each titled "Penile Prosthesis with Improved Tubing Junction".

Rear tips of known IPPs have typically embodied geometries or "profiles" that are relatively high, in that the strain relief portions and tubing junctions may together form a significant elevation or acute angle relative to a longitudinal axis through the cylinder and the rear tip. Additionally, rear tips with their strain relief portions and tubing junctions typically embody relatively rigid and inflexible structures. Thus, rear tips of known IPPs heretofore have, in some cases, presented several drawbacks to physicians who implant them in patients and also to the patients themselves. These deficiencies attributable to a relatively high and rigid rear tip profile have included, for example, a need for substantial anatomical dissection or preparation during implantation surgery, a need for a surgical technique which accommodates implantation of such a device, and post-operative discomfort to the patient due to presence of such a device in the patient's body.

Attempts have been made to solve these aforementioned deficiencies of rear tips through, for example, construction of the strain relief portion and tubing junction in which the tubing was bonded into a pre-molded tubing socket in the strain relief portion using medical grade silicone adhesive. However, such constructions may be relatively inefficient and costly to produce, and may still not satisfactorily mitigate the problems of a relatively high and rigid rear tip profile. Further attempts to mitigate these problems have been proposed through rear tip constructions as described in, for example, the aforementioned U.S. Pat. Nos. 6,808,490 and 7,169,103 to Ling, et al. These publications teach rear constructions utilizing "compound curves" and "keyholes" to provide a device that may be "easier to implant and reduce trauma [by providing] a smaller effective width [or profile] during implantation, after implantation, or both." However, these constructions may also be relatively inefficient and costly to produce, and may not satisfactorily mitigate the aforementioned problems.

Thus, an unmet need has existed for a low profile rear tip for IPPs that may overcome deficiencies of known devices. For example, such a low profile rear tip may be easier to surgically implant when compared to known rigid, high profile rear tips for IPPs. Also, such a low profile rear tip may mitigate post-operative discomfort to the patient when compared to known rigid, high profile rear tips for IPPs. Further, such a low profile rear tip may be relatively more efficient and less costly to produce than known rigid, high profile rear tips for IPPs.

To accomplish these objectives, these rear tips could be constructed with a novel and heretofore unknown profile that is relatively low when compared to known devices, by integrally constructing the strain relief portion and tubing junction as a "one-piece" component, thereby promoting a relatively low profile as desired while also reducing production costs as compared to known devices.

SUMMARY OF THE INVENTION

In accordance with basic aspects of the present invention, a low profile rear tip for inflatable penile prostheses comprises a proximal end portion, and a distal end portion that is capable of being coupled to a cylinder of an IPP along a major longitudinal axis between the proximal end portion, the distal end portion, and the cylinder. A fluid chamber is provided in the distal end portion, in fluid communication with the cylinder. A fluid conduit is integrally formed with the distal end portion, having a minor longitudinal axis and being in fluid communication with the fluid chamber in the distal end portion, wherein an angle between the minor longitudinal axis and the major longitudinal axis does not exceed 5 degrees.

Also in accordance with basic aspects of the present invention, a method of manufacturing a low profile rear tip for inflatable penile prostheses comprises steps of making a mold in a shape of the aforementioned low profile rear tip for IPPs, filling the mold with a selected semi-liquid material, curing the semi-liquid material, and removing the low profile rear tip thereby created from the mold.

DETAILED DESCRIPTION OF THE INVENTION

Figure 1:
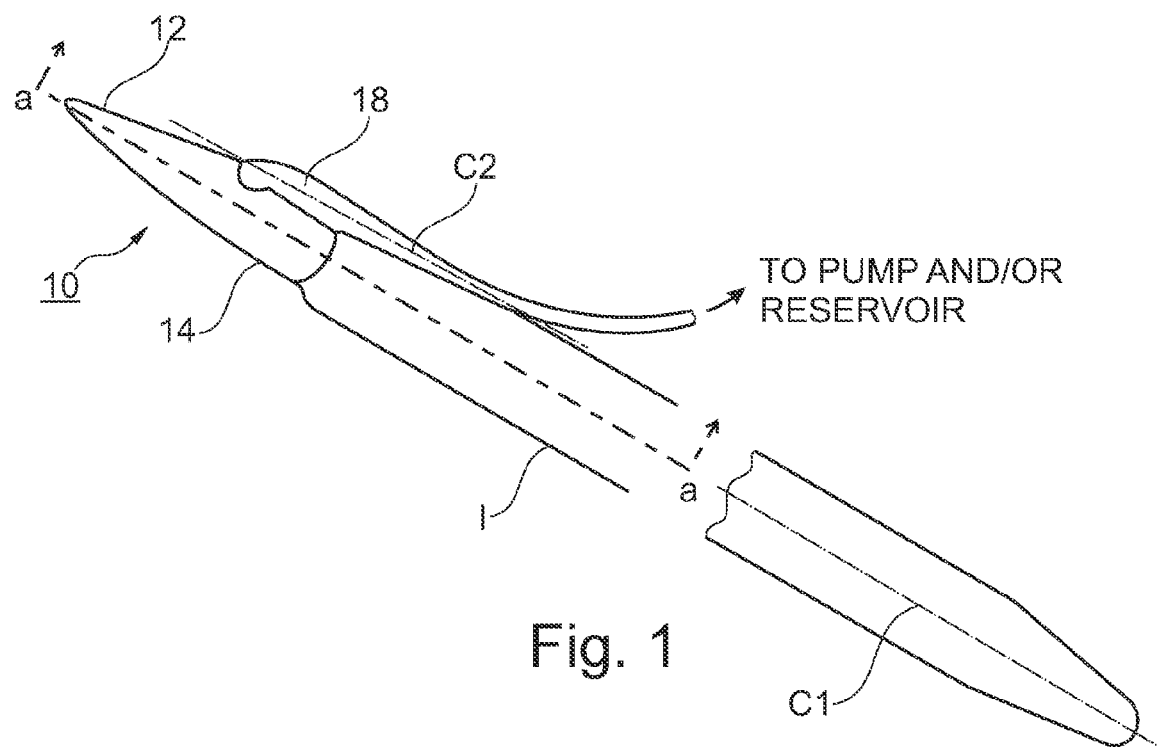
FIG. 1 is a perspective illustration of an example of a low profile rear tip for inflatable penile prostheses of the present invention, depicted as connected to an inflatable penile prosthesis cylinder.
Figure 1A:
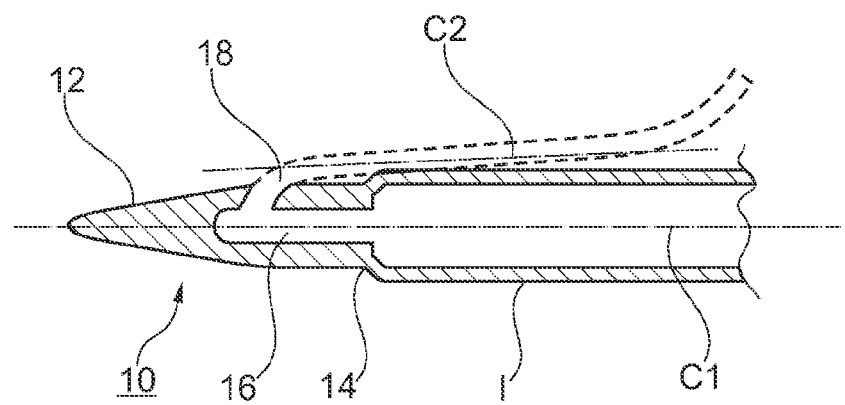
FIG. 1a is a cross-sectional view of the example of a low profile rear tip for inflatable penile prostheses shown in FIG. 1, taken along reference line a-a.

Illustrated in FIGS. 1 and 1a is an example of a low profile rear tip 10 (hereinafter, "rear tip 10") for inflatable penile prostheses of the present invention, depicted as being connected to an IPP cylinder I. In this example, rear tip 10 could include a proximal end portion 12, a distal end portion 14 capable of being coupled to cylinder I along a major longitudinal axis C1 between proximal end portion 12, distal end portion 14, and cylinder I. Rear tip 10 could also include a fluid chamber 16 in distal end portion 14, with chamber 16 being in fluid communication with cylinder I. Rear tip 10 could further include a fluid conduit 18 having a strain relief portion and a tubing junction, integrally formed with distal end portion 14. Fluid conduit 18 could have a minor longitudinal axis C2, and be in fluid communication with fluid chamber 16 in distal end portion 14. Rear tip 10 could be constructed so that an elevation or angle between minor longitudinal axis C2 and major longitudinal axis C1 does not exceed 5 degrees.

Rear tip 10 could be constructed using any suitable techniques as will be described below; and fluid conduit 18 could incorporate, at least in part, kink-resistant tubing.

It is to be appreciated that, as shown particularly in cross-sectional drawing 1a, a low profile rear tip for inflatable penile prostheses of the present invention embodies a relatively low profile as opposed to the high profiles of heretofore known devices. In an example of this configuration, an angle between axes C1 and C2 could be, advantageously, negligible as a result of the aforementioned integral formation of distal end portion 14 with fluid conduit 18 that provides both a strain relief portion and a tubing junction in rear tip 10.

Although not illustrated, it is to be understood that a low profile rear tip of the present invention, as represented by example rear tip 10, could be manufactured using any suitable material and fabrication techniques. For example, a mold could be made in a shape of rear tip 10. The mold could be filled with a selected semi-liquid material. The semi-liquid material could then be cured, and rear tip 10 thereby created could then be removed from the mold and coupled to cylinder I. Manufacturing of the IPP could then be completed as desired. The semi-liquid material could be, as desired or suitable for a particular manufacturing process, a medical grade silicone elastomeric material or an elastic-thermoplastic resin. It is to be appreciated that, although again not illustrated herein, example rear tip 10 could also be manufactured using any suitable fabrication techniques such as transfer molding or injection molding.

It is to be appreciated from the foregoing disclosure that the present invention uniquely and advantageously satisfies the long-felt need for a low profile rear tip for IPPs that are easily implantable device in implantation surgery and give patient comfort.

It is to be understood that novel aspects of the present invention regarding IPPs per se will be appreciated by those in the surgical arts to be capable of use in, and beneficial to, virtually any implantable devices involving tubing junctions—even those outside of IPP technologies.

While the present invention has been particularly shown and described with reference to the accompanying specification and drawings, it will be understood however that other modifications thereto are of course possible; and all of which are intended to be within the true spirit and scope of the present invention. It should be appreciated that (i) components, dimensions, shapes, and other particulars of example embodiments of the invention aforedescribed may be substituted for others that are suitable for achieving desired results, (ii) various additions or deletions may be made thereto, and (iii) features of the foregoing examples may also be made in combinations thereof. It is also to be understood in general that any suitable alternatives may be employed to provide the low profile rear tip for inflatable penile prostheses of the present invention.

Lastly, of course, the choice of compositions, sizes, and strengths of various aforementioned elements of the present invention are all a matter of design choice depending upon intended uses thereof.

Accordingly, these and other various changes or modifications in form and detail of the present invention may also be made therein, again without departing from the true spirit and scope of the invention as defined by the appended claims.

What is claimed is:

1. An implantable penile prosthesis attachable to a pump and a reservoir, the penile prosthesis comprising:
    a distal part formed by a rear tip that is connected to a proximal part formed by a cylinder, the cylinder oriented on a first longitudinal axis, and a distal portion of the rear tip forming a fluid chamber that is in fluid communication with the cylinder; and
    a fluid conduit providing a strain relief portion and a tubing junction integrally formed with the distal portion and communicating with the fluid chamber in the rear tip, the strain relief portion of the fluid conduit has a bore disposed on a second longitudinal axis, where the second longitudinal axis forms an acute angle relative to the first longitudinal axis, and the acute angle has a measurement that does not exceed 5 degrees;
    wherein an exterior surface of the rear tip, between the tubing junction and the cylinder, provides the distal portion of the rear tip with a constant outer diameter.

2. The penile prosthesis of claim 1, wherein the exterior surface of the rear tip tapers toward the first longitudinal axis of the cylinder proximal to the tubing junction.

3. The penile prosthesis of claim 1, wherein the exterior surface of the rear tip tapers linearly toward the first longitudinal axis of the cylinder proximal to the tubing junction.

4. The penile prosthesis of claim 1, further comprising: a front end portion connected to a front end of the cylinder.

5. The penile prosthesis of claim 1, wherein the acute angle is about zero degrees.

6. The penile prosthesis of claim 1, further comprising tubing connecting the fluid conduit to a pump.

7. The penile prosthesis of claim 1, further comprising tubing connecting the fluid conduit to a reservoir.

8. The penile prosthesis of claim 1, wherein the strain relief portion is fixed relative to the first longitudinal axis of the cylinder.

9. The penile prosthesis of claim 1, wherein the strain relief portion and the distal portion of the rear tip are molded together with the strain relief portion integrated into the distal portion of the rear tip.

* * * * *